United States Patent [19]

Tsai et al.

[11] Patent Number: 5,464,760

[45] Date of Patent: Nov. 7, 1995

[54] FERMENTATION AND RECOVERY PROCESS FOR LACTIC ACID PRODUCTION

[75] Inventors: Shih-Perng Tsai, Downers Grove; Seung H. Moon, Westmont, both of Ill.; Robert Coleman, Lansing, Mich.

[73] Assignee: University of Chicago, Chicago, Ill.

[21] Appl. No.: 965,830

[22] Filed: Oct. 23, 1992

Related U.S. Application Data

[63] Continuation-in-part of Ser. No. 504,223, Apr. 4, 1990, abandoned.

[51] Int. Cl.$^6$ .................................. C12P 7/56; C13K 1/06
[52] U.S. Cl. ............................ 435/139; 435/853; 127/42; 536/124
[58] Field of Search ........................... 536/1.1, 127, 124, 536/127; 127/1, 23, 24, 34, 38, 42; 435/139, 853

[56] References Cited

U.S. PATENT DOCUMENTS

| | | |
|---|---|---|
| 1,569,221 | 1/1926 | Faithfull ........................ 435/139 |
| 2,588,460 | 3/1952 | Aries et al. ..................... 435/139 |
| 3,125,494 | 3/1964 | Snell et al. . |
| 3,202,705 | 8/1965 | Powell et al. ................... 435/139 |
| 3,337,414 | 7/1967 | Wilson . |
| 3,410,755 | 11/1968 | Etchells et al. ................. 435/139 |
| 3,494,832 | 2/1970 | Florent et al. . |
| 3,897,305 | 7/1975 | Hurst . |
| 3,910,820 | 10/1975 | Holt et al. . |
| 4,361,651 | 11/1982 | Keim . |
| 4,698,303 | 10/1987 | Bailey et al. ................... 435/139 |
| 4,771,001 | 9/1988 | Bailey . |
| 4,813,997 | 3/1989 | Kinnersley et al. . |
| 4,882,277 | 11/1989 | Czytko et al. .................. 435/136 |
| 4,885,247 | 12/1989 | Datta ............................. 435/139 |
| 5,002,881 | 3/1991 | Van Nispen et al. ............ 435/139 |
| 5,071,754 | 12/1991 | Walkup et al. .................. 435/135 |

OTHER PUBLICATIONS

Tiwari et al., "Lactic Acid Production From Molasses by Mixed Population of Lactobacillus Bulgaricus", and L. Delbruecki, Proc. Nat. Acad. Sci. India, 47(a), II 1977.

Coleman, et al., "Bio- and Photodegradable Copolymers Derived From Low-Cost Feedstocks", American Institute of Chemical Engineers, Aug. 21, 1989.

Coleman, et al., "Transformation of High-Carbohydrate Food Wastes Into Degradable Plastics", 74th Annual Meeting, American Association of Cereal Shemists, Oct. 29, 1989.

Schertz, et al., "Design and Construction of Degradable Plastics Derived From Inexpensive Carbon Sources", ASME Winter Meeting, Dec. 19, 1989.

*Primary Examiner*—Jeffrey Mullis
*Attorney, Agent, or Firm*—Reinhart, Boerner, Van Deuren, Norris & Rieselbach

[57] ABSTRACT

A method of converting starch to glucose and fermenting glucose to lactic acid, including simultaneous saccharification and fermentation through use of a novel consortium of bacterial strains.

16 Claims, 2 Drawing Sheets

FERMENTATION AND RECOVERY PROCESS FOR LACTIC ACID PRODUCTION

The United States Government has rights in this invention pursuant to Contract No. W-31-109-ENG-38 between the U.S. Department of Energy and The University of Chicago, representing Argonne National Laboratory. This is a continuation-in-part of application Ser. No. 07/504,223, filed Apr. 4, 1990, now abandoned.

This invention generally relates to the bioconversion of industrial food waste containing starch to lactic acid suitable for conversion to photodegradable or biodegradable plastics. More particularly, this invention relates to an overall process for the conversion of high carbohydrate containing materials such as potato waste, cheese whey or the like into lactic acid which is thereafter polymerized to produce various degradable plastics. Cheese whey permeate which contains lactose rather than starch can also be used with slight modifications.

A large supply of readily fermentable and generally non-toxic food waste provides an abundant and concentrated source of carbon and nitrogen for various aerobic and anaerobic bacteria. In the United States alone, totals for corn and potato waste streams are large, about 5.0 million tons per year for potato alone, and other food streams also contain ideal substrates for enzyme and/or microbiological conversion to useful compounds. Lactic acid is one of the products which can potentially be extremely useful in industry. From lactic acid can be made various degradable plastics. Degradable plastics will assume an increasingly important role in replacing or partially replacing various plastic materials which remain in the environment or degrade so slowly that for all practical purposes do not degrade in land fills. Lactic acid can be bioconverted directly from cheese whey permeate, cane and beet sugars using various lactic acid bacteria, such as Lactobacilli, in relatively high yields or indirectly by first hydrolyzing the starch in corn, potato or rice followed by bioconversions with lactic acid bacteria. Lactic acid and its sodium or calcium salts are non-toxic and are classified as GRAS (Generally Recognized As Safe) by the FDA.

Accordingly it is one object of this invention to provide an improved method of fermentation using a mixed culture to produce a highly stereospecific L-lactic acid. The mixed culture, code-named LBM5, is preferably composed of *L. delbrueckii* subsp. *lactis* ATCC 12315, *L. casei* NRRL B-1445, *L. delbrueckii* NRLL B-445, *L. helveticus* NRRL B-1937, and *L. casei* NRRL B-1922. Acclimation techniques were used to improve growth temperature and product tolerance of the strains before the mixed culture was composed. Individually, *L. delbrueckii* subsp. *lactis* ATCC 12315 was the most preferred strain in terms of batch fermentation rate. The mixed culture LBM5 exhibited a reduced batch fermentation time compared with *L. delbrueckii* subsp. *lactis* ATCC 12315. This difference is likely due to symbiosis. The mixed culture LBM5 was also found to be able to maintain cell viability at high lactate concentration.

It is a further object of the invention to provide a new method for simplified bioconversion of starch into lactic acid by effecting a simultaneous saccharification and fermentation. The starch-containing material, such as a homogenized potato waste, is first liquefied by alpha-amylase enzyme at an elevated temperature in the range of from about 90° C. to about 130° C. for a time no less than about 15 minutes. The step also sterilizes or pasteurizes the material to control microbial contamination during fermentation. The temperature of the liquefied material is then lowered to about 42° C. and the pH adjusted to about 5.5. Then glucoamylase enzyme, lactic acid bacteria and nutrients are added at effective concentrations to effect simultaneous conversions of liquefied starch to glucose and glucose to lactic acid, catalyzed by glucoamylase and the bacteria, respectively. The combined process reduces the total process time for conversion of starch to lactic acid. It can also reduce the capital and operating costs of the process. Simultaneous saccharification and fermentation can occur only if both the enzyme and the microbe have sufficient activities at the process temperature and pH. Also, the microorganism should not have adverse effects on the enzyme and vice versa. Many microorganisms possess proteases that can damage the exogenous enzymes. Lactic acid bacteria have little proteolytic activities and our laboratory tests showed that the activity of lactic acid bacteria can be maintained in the presence of added glucoamylase.

It is a further object of the invention to provide an improved method using a hydrolyzed (liquefied and saccharified) starch as a feed for fermentation. The hydrolyzed starch, such as the potato hydrolysate prepared from potato wastes or the commercially available glucose syrup from corn processors, normally contains up to 5% of impurity sugars such as maltose and oligosaccharides. The impurity sugars tend to remain unutilized at the end of fermentation and cause difficulties in product purification. This invention provides a method of reducing the broth impurity sugar levels by adding carbohydrases during fermentation. Carbohydrases, such as maltase and glucoamylase, can convert maltose and oligosaccharides into glucose which is readily consumed by the microorganisms. Also, with this invention the fermentation process can accept a "bad" (incompletely hydrolyzed) batch of material, which contains higher than normal levels of sugar impurities and is normally unsuitable for fermentation. This will allow one to use less stringent quality control methods and criteria for the hydrolysis process and thus improve the economics of the whole process.

It is still another object of the invention to provide a novel method of rapid starch fermentation by adding nutrients to the carbon source (e.g., potato hydrolysate). A nutrient formulation that has yielded satisfactory results comprises the following: 2 g/L $KH_2PO_4$, 5 g/L sodium acetate, 10 g/L trypticase peptone, 5 g/L yeast extract, 3 g/L tryptose, 1 ml/L Tween 80, 0.573 g/L $MgSO_4.7H_2O$, 0.034 g/L $FeSO_4 7H_2O$, and 0.12 g/L $MnSO_4$. Another satisfactory formulation, code-named STLM-B comprises the following: 3 g/L $KH_2PO_4$, 3 g/L $K_2HPO_4$, 1 g/L sodium acetate, 10 g/L trypticase peptone, 5 g/L yeast extract, 3 g/L tryptose, 1 ml/L Tween 80, 229 mg/L L-cystein-$HCl.H_2O$, 0.573 g/L $MgSO_4 7H2O$, 0.034 g/L $FeSO_4 7H_2O$, and 0.12 g/L $MnSO_4$. Alternatively, corn steep liquor, a much less expensive source of nutrients, has been found to be satisfactory at no more than 5% concentration in lieu of the nutrient supplements set forth hereinbefore.

It is yet another object of the invention to provide an improved continuous process. Many industrial fermentation processes are operated in the batch mode due to the difficulties in maintaining a proper physiological state and cultural purity (i.e., free of microbial contamination) for a continuous culture. Lactic acid fermentation, however, in the manner of the invention, is a good basis for the continuous process. Homofermentative lactic acid bacteria produce lactic acid as the sole metabolite during the stationary, as well as the growth phase. Therefore, maintaining the cultural physiological state is not critical. Also, contamination is usually not a problem for lactic acid fermentation due to the relatively high temperature, low pH and high lactate concentrations of the process. The configuration of the continuous bioreactor system can be a single stage or a two-stage bioreactor. Cell recycle, effected by a membrane filter or a continuous centrifuge, would be preferred to increase cell concentration and thus increase the volumetric productivity of the bioreactor. Although a single stage system is more simplistic, a two-stage system may favor cell viability at high product concentrations, at the expense of increased system complexity. If a two-stage system is employed, it would be particularly advantageous to operate the system in a manner that the lactate concentration in the first stage is below the critical concentration that would inhibit cell growth, and the recycled cell mass from the second stage is fed into the first stage.

It is still a further object of the invention to provide a novel method of purified lactic acid recovery from the fermentation broth containing sodium lactate using electrodialysis. The electrodialytic cell is divided by ion-exchange membranes into separate compartments. In the presence of an electrical field, lactate ions in the fermentation broth migrate through an anion-exchange membrane into a product compartment and are recovered as a free acid solution and sent for further processing. Sodium ions, at the same time, migrate through a cation-exchange membrane, resulting in a sodium hydroxide stream which can be recycled for pH control in fermentation or other uses in the plant. The hydrogen and hydroxide ions needed for the balance of electrical charges in the lactic acid and sodium hydroxide compartments can be provided either by electrolysis of water in the electrode compartments in a conventional electrodialysis system or by water splitting in the bipolar membrane. Primary considerations in the electrodialysis process include: membrane transfer area requirement, energy consumption, yield of recovery, lactic acid purity and lactic acid concentration. The obtainable lactic acid purity is affected by the characteristics of the anion-exchange membrane. In general, a "tighter" membrane such as Ionics Corp.'s 204-UZRA-412 or equivalent conventional membrane is preferred for high lactic acid purity, although other membranes, such as, Ionics' 103-QZL-386 are also satisfactory. The lactic acid product concentration can be affected by manipulating the volume ratio of the feed and product streams. The membrane transfer area requirement (capital costs) and the energy consumption (operating costs) are inversely correlated. In general, the optimal conditions need to be determined case by case with considerations of the economics of the particular plant.

It is yet a further object of the invention to provide a further purified lactic acid recovered from electrodialysis. The electrodialysis product can be concentrated to about 35% by vacuum evaporation at 60°–70° C., resulting in a concentrated crude acid. Lactic acid can be further purified by liquid-liquid extraction followed by back-extraction. The process involves contacting the crude lactic acid with an extractant (such as a tertiary amine in a water-immiscible organic solvent) and back-extracting the lactic acid from the extractant using a concentrated alkali solution (such as sodium hydroxide) resulting in a lactate salt (e.g., sodium lactate). The lactate solution can then be processed by electrodialysis to recover the alkali solution and a purified lactic acid. The process effectively reduces the level of total impurity which can interfere with certain end applications, such as synthesis of poly-lactic acid.

It is still another object of the invention to provide a novel extraction process using an electrodialysis-processed and concentrated crude lactic acid stream. To extract lactic acid from a fermentation broth, it is necessary to acidify the broth. In the conventional processes, this is done by addition of a mineral acid, such as sulfuric acid, or by ion-exchange. In the former case, the mineral acid is co-extracted with lactic acid and contaminates the product. In both cases a large volume of the salt solution is generated, which causes a waste disposal problem. Electrodialysis acidifies the fermentation broth without generating these problems. Also, extraction of the acidified fermentation broth directly often suffers from phase separation problems due to formation of precipitates at the interface or stable emulsion caused by certain impurities. Electrodialysis removes many impurities and thus eliminates the phase separation problems. In addition, extracting from a concentrated (e.g., lactic acid) stream, compared to a dilute stream (e.g., an acidified fermentation broth containing about 10% lactic acid) has other advantages, such as, generating a smaller volume of a solvent-contaminated spent broth wastestream and ease of operation.

It is another object of this invention to provide an efficient process for producing lactic acid of sufficient purity to make a degradable plastic of lactide polymers and copolymers from a renewable biomass material in a sufficiently short process time to render the entire method economically viable.

Another further object of the invention is to provide a process for converting industrial food waste to glucose and then to lactic acid by the use of both enzyme and microbiological action, wherein the processing time to produce over 90% glucose is reduced to less than ten hours and the subsequent process time is less than about forty-eight hours to produce lactic acid from the glucose.

Yet another object of the invention is to convert industrial starchy waste into lactic acid while providing a glucose intermediate product which is substantially devoid of microbial contamination.

Other objects and advantages of the invention are described in the Detailed Description and the Drawings provided herein.

DETAILED DESCRIPTION OF THE PREFERRED EMBODIMENTS

Figure 1A:
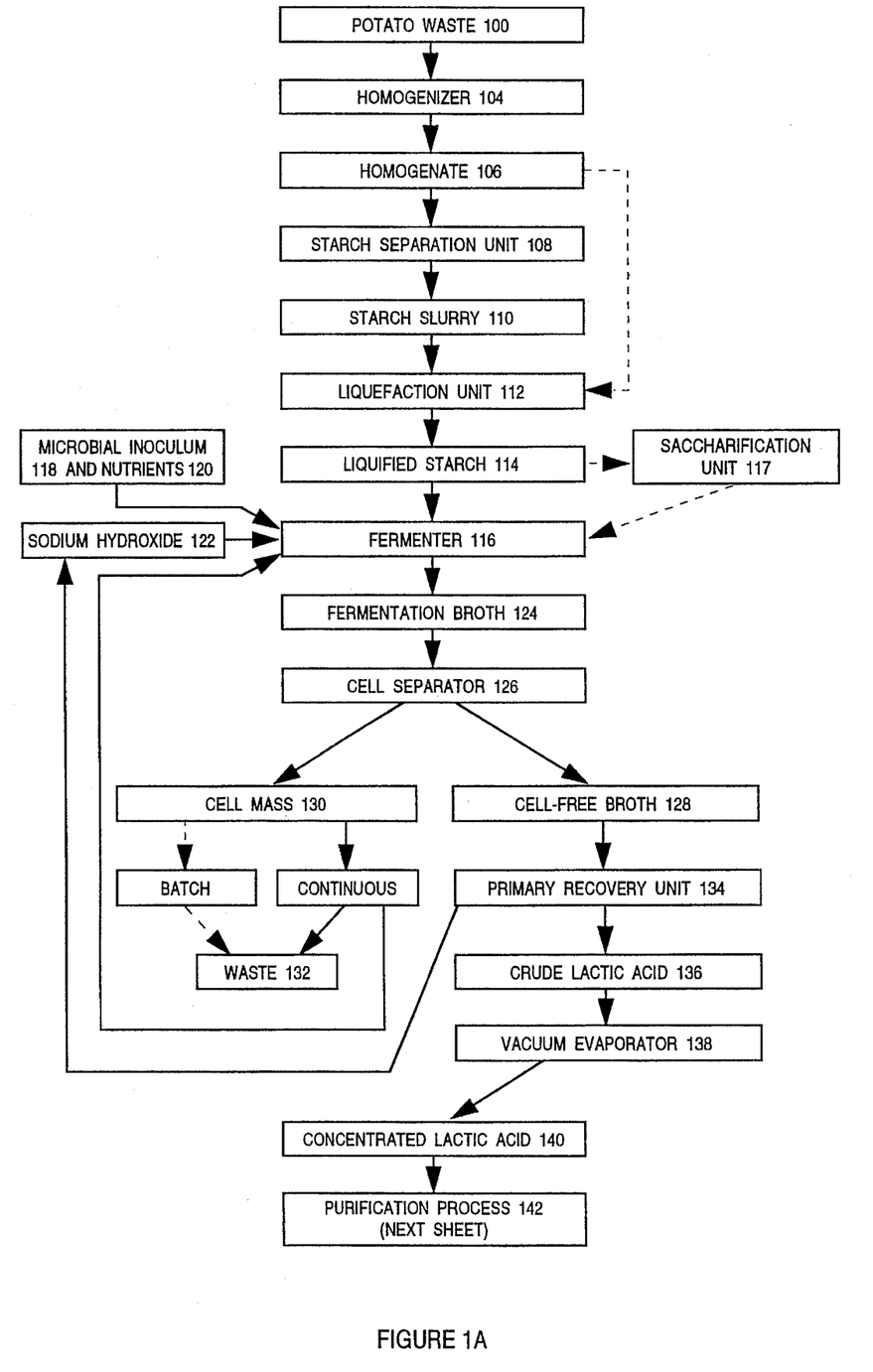
FIGS. 1A and 1B illustrate process flow diagrams in accordance with the invention.
Figure 1B:
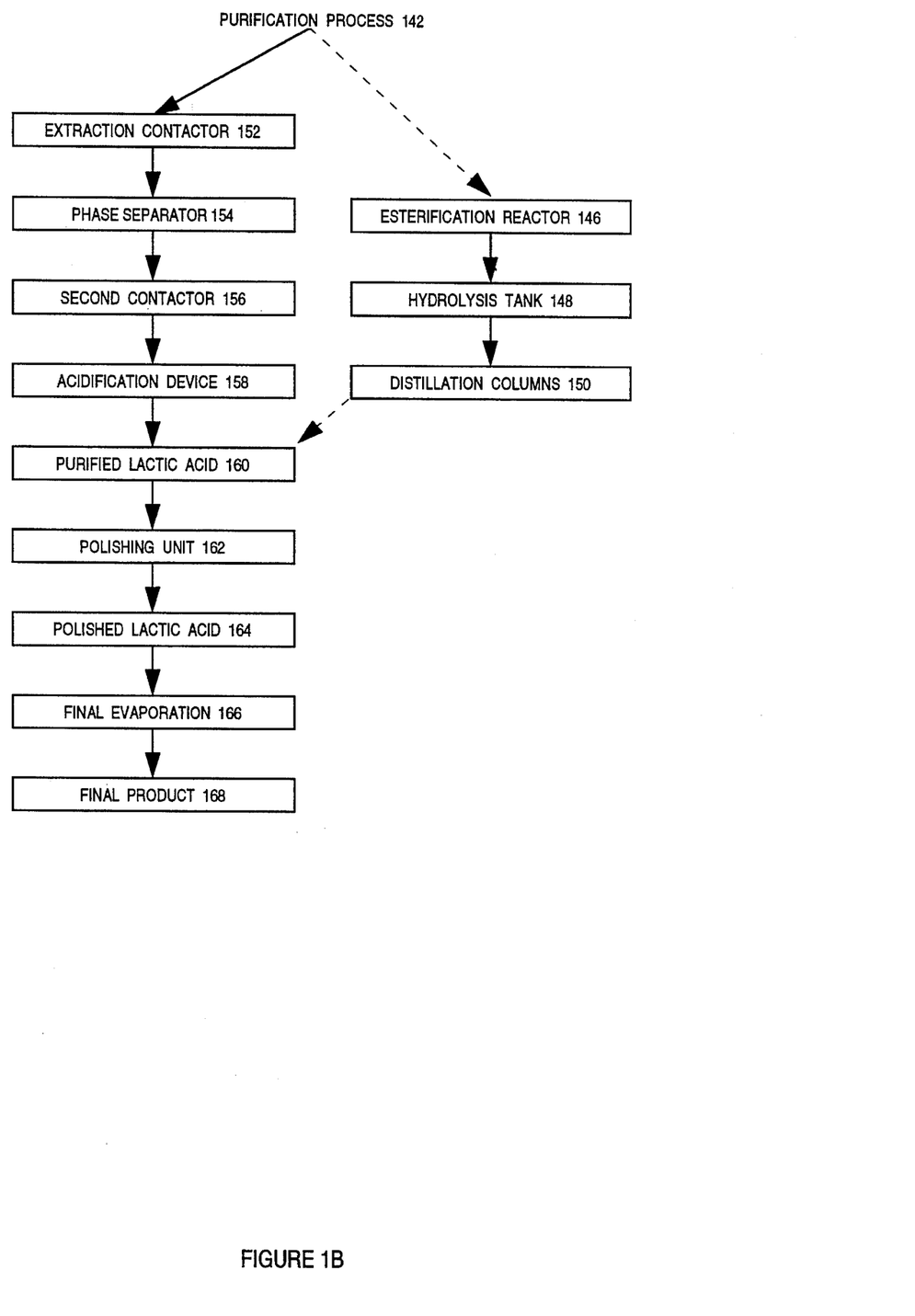

A flow diagram of the preferred process of converting the potato waste to high purity lactic acid is given in FIGS. 1A and 1B. The potato waste 100 is fed to the homogenizer 104 which can be a hammer mill or Rietz mill, to produce a potato waste homogenate 106. Separation of the potato starch from other components of the homogenate, if desired, is performed in the optional starch separation unit 108, which includes a shaker screening and a settling tank or a centrifugal separator. The starch slurry 110 (or the homogenate 106 directly, if starch separation is omitted) is pumped to the liquefaction unit 112 to produce a liquefied starch 114, which is charged to the fermenter 116 for simultaneous saccharification and fermentation.

The potato waste stream includes any high carbohydrate waste from a potato processing plant such as french fry plant, potato chip plant or the like and may include potato peel as well as other waste products. The potato waste, however, must be ground, blended or homogenized or otherwise size reduced by industrial blending and thereafter diluted with suitable water or deionized water until the mixture is essentially uniform. FIG. 1, shows a combined processing step lasting from approximately 15 to about 30 mixtures. This step, which combines gelatinization and liquefaction of potato starch, the potato waste pH is adjusted in the range of from about 4 to about 7 but the preferred pH is about 5. Hydrochloric acid may be used to adjust the pH to 5 if the pH of the potato waste is somewhat higher. To this pH adjusted material is added an effective amount of α-amylase enzyme along with a stabilizing material in the form of calcium chloride. The α-amylase enzyme is added in a concentration of from about 1x to about 100x, wherein x=(30 units of α-amylase enzyme)/(gram of dry substance of starch-containing material). The preferred amount of α-amylase, depending to some extent upon the starting material, is about 10x. The calcium chloride is added in the range of from about 50 ppm to about 400 ppm with the preferred concentration being about 200 ppm. The pH, although preferred in this step to be about 5, may be in the range of from about 4–7, but is better maintained in the range of about 4.5 to about 6.5. In order to avoid readjustment of pH during later processing, it is preferred that the pH in the beginning α-amylase treatment remain in the range of from about 4.5 to about 5.5 with a pH of 5 preferred.

After the calcium chloride and the α-amylase have been added to the starch and thoroughly mixed, the material is heated under pressure. This is a crucial step and one which has been found to greatly reduce the processing time and also results in a non-microbial contaminated product. Specifically, it is preferred that the starch-containing material be uniformly exposed to an elevated temperature in the range of from about 90° C. to about 130° C. while the pressure is maintained at least at 15 psi for a time not less than about 15 minutes and preferably in the range of from about 20 to about 30 minutes. While the foregoing temperature range of 90° C. to 130° C. is available, it has been found that a temperature of about 121° C. in combination with a 20 minute time span wherein the pressure is maintained at 15 psi has produced superior results. This process is important because it results in a material which has minimal microbiological activity.

Thereafter, the material is cooled to a second temperature in the range of from about 50° to about 70° and the pH is adjusted to below 6.5, if in fact it was higher for the α-amylase portion of the treatment. It has been found that the α-amylase processing for liquefaction of the starch may be accomplished at a pH as high as 7, but glucoamylase loses activity at a pH of greater than about 6.5. Accordingly, even if the initial portion of the process is conducted at a high pH, the glucoamylase is only effective at a lower pH. For this reason, it is preferred that the pH for all the enzymatic steps be maintained at about 5, even though the optimal pH for the glucoamylase enzyme is about 4.3.

After the temperature has been lowered the range of about 50° C. to about 70° C. with a temperature of about 60° C. being preferred, the glucoamylase is added to the mixture in awl effective amount, preferably at a concentration in the range of from about 0.5x to about 100x where 1x=[(13.44 unit-hour of glucoamylase)/(gram of dry substance of starting starch containing material)]÷total hours of incubation. The incubation time is preferably in the range of from about 4 to about 8 hours with the shortest time for to conversion to 90% to glucose being preferred. That is if the desired percent conversion occurs in the four hour time frame, then there is no substantial advantage to incubating for a longer period of time. In general, satisfactory results of over 90% conversion of the available starch to glucose has occurred in the time range of under 10 hours for the total process, with the glucoamylase digest taking approximately 4 to 8 hours. The glucoamylase portion of the conversion is conducted at atmospheric pressure. The mixture should be at a temperature of 60° C. or less when the glucoamylase is added, otherwise the glucoamylase enzyme is unstable and may lose activity. For instance, 50° C. is also satisfactory, and while a temperature of 70° C. may be acceptable, lower temperatures are preferred. When it is desired to stop the action of the glucoamylase, the mixture is simply boiled thereby decomposing the glucoamylase and halting the saccharification reaction.

After the enzymatic hydrolysis reactions, the potato hydrolysate contains solids as well as a liquid portion containing glucose. The potato hydrolysate is passed through a filtration device wherein the solids are separated from the glucose-containing filtrate. To the filtrate from the filtration station is added nutrients to facilitate fermentation of the glucose to lactic acid.

In order for the fermentation to take place in a suitable time frame, the filtered potato hydrolysate containing the glucose must have certain nutrients in order to promote the bacterial growth necessary for the fermentation to take place in an acceptable time frame. In general, in batch tests there has been added monobasic potassium phosphate at 2 grams per liter, sodium acetate at 5 grams per liter, trypticase peptone at 10 grams per liter, tryptose at 3 grams per liter, yeast extract at 5 grams per liter, Tween 80 at 1 milliliter per liter, magnesium sulfite.7 $H_2O$ at 0.575 grams per liter, iron sulfate.7 $H_2O$ at 0.034 grams per liter and manganese sulfate.$2H_2O$ at 0.12 grams per liter. While these nutrient additives are adequate and satisfactory on a bench scale or laboratory test sizes, it is understood that in a production scale environment, inexpensive nutrient sources such as corn steep liquor can be used in lieu of the nutrient supplements above set forth.

As a variance of the process, if a separate saccharification step is desired (note dotted lines on flowchart) the liquefied starch 114 is sent to a saccharification unit 117 to produce a glucose syrup before it is fed into the fermenter 116. Also fed into the fermenter 116 are the microbial inoculum 118 and nutrients 120. During fermentation, a sodium hydroxide solution 122 is added to the fermenter for pH control. The fermentation broth 124 containing cell mass and sodium lactate, is processed by a cell separator 126 which can be a centrifuge or a membrane micro- or ultra-filtration device, to produce a cell-free broth 128 containing sodium lactate solution and a cell mass concentrate 130. The fermenter and separator units can be operated in a batch or continuous mode. In the batch mode, all the cell mass concentrate 130 goes to waste 132. In the continuous mode, part of the cell mass concentrate 130 is recycled to the fermenter 110 and part of it goes to waste 132. If desired, a filtration device can be used to further recover the product (sodium lactate solution) from the wastestream 132. The cell-free broth 128 is fed to the primary recovery unit (electrodialysis) 134 to generate a sodium hydroxide solution 122 which is recycled for fermentation pH control, and a crude lactic acid 136 which is further concentrated in a vacuum evaporator 138.

The concentrated crude lactic acid 140 produced from the vacuum evaporator 138 is further processed in the purification process 142 to produce a purified lactic acid 160. The purification process 142 can be esterification or extraction. If esterification is used (see dotted lines on flow diagram) the process includes an esterification reactor 146, a hydrolysis tank 148, and distillation columns 150 for separation of lactic acid. If extraction is used, the process includes a contactor 152 for extraction, a phase-separator 154, a second contactor 156 for back-extraction, and an acidification device 158. The purified lactic acid 160 is fed into the polishing unit 162, which may include treatment by ion-exchange resins and activated carbon. The polished lactic acid 164 is further concentrated in the final evaporation 166 to generate the final product 168, a high purity lactic acid.

The following non-limiting samples illustrate various methods of preparation characteristic of the inventions.

EXAMPLE 1

Five lactic acid bacterial strains, *L. delbrueckii* subsp. *lactis* ATCC 12315, *L. casei* NRRL B-1445, *L. delbrueckii* NRRL B-445, *L. helveticus* NRRL B-1937, and *L. casei* NRRL B-1922, were mixed in equal parts to form the mixed culture code-named LBM5. A batch fermentation with STLM-B medium was carried out in a 3-L fermenter. An inoculum grown in the shake-flask for about 12 h was used at 10% (v/v) inoculum size. The fermentation temperature was controlled at 42° C. The pH of the medium was 6.3 initially and was allowed to drop to 5.5 as lactic acid was produced. Further decrease of pH was prevented by addition of 10 N NaOH. The fermentation, with an initial glucose concentration of 110g/L, was completed (i.e., glucose was consumed to less than 0.1 g/L) in 24.5 h, resulting in a lactic acid concentration of 99.2 g/L and a batch productivity of 4.0 g/(L·h). In comparison, a batch fermentation under similar conditions using the best constituent pure culture, *L. delbrueckii* subsp. *lactis* ATCC 12315, resulted in a batch productivity of 3.1 g/(L·h). The mixed culture was found to perform unexpectedly and significantly better than the best single constituent strain. Symbiotic interactions appeared to exist in the mixed culture.

EXAMPLE 2

In another batch fermentation of LBM5 performed as in Example 1, the inoculum was cultivated in a seed bioreactor at controlled pH of 5.5 to maintain a highly active state. The fermentation progressed rapidly and the initial 110 g/L of glucose was completely utilized in 18.6 h, resulting in further improved batch productivity of 5.3 g/(L·h). In both fermentations, the mixed culture exhibited a high stereospecificity and 98% of the lactic acid produced was the L-lactic acid.

EXAMPLE 3

To determine the effect of lactic acid concentration on cell viability, the mixed culture LBM5 was tested in a chemostat at a moderate dilution rate (0.05 h$^{-1}$) and at high lactic acid concentrations (80 to 110 g/L). Lactic acid, the fermentation product, was added in the feed medium to obtain a high product concentration in the bioreactor. One medium tank (Medium A), contained STLM-B medium with 105 g/L of glucose. The second medium tank (Medium B) contained STLM-B medium that was devoid of glucose, but contained 105 g/L of lactic acid. Initially the bioreactor containing the regular STLM-B medium was operated in the batch mode for 28 h to accumulate cell mass. In the continuous mode, the total feed rate was maintained at 25 ml/h while the individual feed rates of Medium A and Medium B were varied. Consequently, the effective lactic acid concentration in the feed varied in the range of 0 to 67.2 g/L. The bioreactor agitation speed was 80 rpm, the working volume was 550 ml, and the pH was controlled at 5.5 with 10 N NaOH solution. The effective dilution rate, taking into account the rate that NaOH was added, varied between 0.045 and 0.05 h$^{-1}$, depending on the lactic acid production rate.

The steady-state chemostat results are summarized in Table 1. A considerable number of viable cells were alive at 106.6 g/L of lactic acid at 42° C. The cells were growing continuously under this condition and did not wash out from the bioreactor. The results imply that cell activities (cell growth and lactic acid production) were maintained at this high lactic acid concentration range.

TABLE 1

| FEED | | BIOREACTOR | | | |
|---|---|---|---|---|---|
| [Lactic Acid] (g/L) | [Glucose] (g/L) | [Lactic acid] (g/L) | [Glucose] (g/L) | OD$_{560}$ | Viable Cells (10$^9$ CFU/ml) |
| 0.0 | 105.0 | 82.9 | 17.2 | 14.2 | 8.0 |
| 33.6 | 71.4 | 90.2 | 6.1 | 12.8 | 7.5 |
| 54.6 | 50.4 | 93.9 | 7.7 | 9.2 | 5.0 |
| 67.2 | 37.8 | 106.6 | 1.3 | 5.9 | 3.4 |

EXAMPLE 4

Five 4-strain subconsortia of LBM5 were evaluated in shake flask experiments for their batch fermentation rate in a CaCO$_3$-buffered STLM-B medium. LBM4, which was LBM5 less *L. casei* NRRL B-1922, was found to perform as well as LBM5 and better than all other 4-strain subconsortia. A batch fermentation of LBM4 was performed in the bioreactor as described in Example 1, using an active inoculum grown at pH 5.5. The fermentation, with an initial glucose concentration of 110 g/L, was completed in less than 23.5 h, resulting in a lactic acid concentration of 100.3 g/L.

EXAMPLE 5

Four flasks (A, B, C, and D) were prepared, each containing 4 g of soluble starch (Mallinckrodt) and 0.3 g of sodium acetate in 100 ml of water. The pH of the solution was adjusted to 5.0 by addition of 5 M HCl. To each flask, 28 µl of an alpha-amylase solution (Enzyme Bio-Systems, G-ZYME G995, nominal activity=4350 U/ml) and 20 µl of 1 M CaCl$_2$ solution were added. The flasks were then autoclaved for 15 min at 121° C. to effect liquefaction of starch.

A nutrient solution, which was prepared at pH 5.9 and was autoclaved separately, was added at 50 ml to each flask, to provide nutrients of PM-C medium. A glucoamylase solution (EBS, G-ZYME G-990, nominal activity=200 U/ml) was added to flasks A, B, and D. 30 minutes later, an inoculum of *L. delbrueckii* subsp. *lactis* was added to flasks A, B, and C. All the flasks were incubated at 42° C. After 48 hours of incubation, the pH and lactic acid concentration were measured for each flask. A GC method was used for lactic acid measurement. The results are summarized in Table 2.

TABLE 2

| Flasks | pH | [lactic acid], g/L | Remarks |
|---|---|---|---|
| A | 3.4 | 14.7 | |
| B | 3.4 | 4.9 | |
| C | 5.2 | 0.0 | no glucoamylase added |
| D | 5.5 | 0.0 | no bacteria added |

Conversion of the liquefied starch to lactic acid occurred only in the presence of both glucoamylase and the bacterial

EXAMPLE 6

2500 g of whole potatoes (obtained from a local supermarket) was blended in a Waring blender and pH adjusted to 5.0. 1500 g of the blended potato was placed in a bioreactor and liquefied by adding 2.1 ml of an alpha-amylase solution (EBS, G-ZYME G995, nominal activity=4350 U/ml where one unit (U) is typically the amount of enzyme which will hydrolyze 10 mg of starch in ten minutes under use conditions) and 1.5 ml of 1 M $CaCl_2$ solution then incubating in an autoclave for 20 min at 121° C. To the liquefied potato, 450 ml of sterile water and 500 ml of a nutrient solution (containing nutrients for 2000 ml of PM-C medium) were added. An 150 ml inoculum of *L. delbrueckii* subsp. *lactis* and 2.0 ml of a glucoamylase solution (EBS, G-ZYME G-990, nominal activity=200 U/ml where one unit (U) is typically the quantity of enzyme that forms 1 mg of dextrose in one minute with soluble starch substrate under standard assay conditions of pH of 4.3 and 60° C.) were added to effect simultaneous saccharification and fermentation at pH 5.5 and 42° C. After 41 hours, 200.3 g of lactic acid was produced.

In parallel, 1000 g of the blended potato was processed via an established enzymatic hydrolysis process. From the 1000 g potato, the process yielded 133.3 g of glucose, which could be converted to 126.6 g of lactic acid if fermented subsequently with a 95% yield. Therefore, the lactic acid yield from the simultaneous saccharification and fermentation was 105% of that from the separate hydrolysis and fermentation process.

EXAMPLE 7

To 1800 g of potato waste, 1.9 ml of 1 M $CaCl_2$ and 2.6 ml of an alpha-amylase solution (EBS, G-ZYME G995, nominal activity=4350 U/ml) were added. The potato waste was then blended in a Waring blender, and its pH was adjusted to 5.0. The potato waste and 600 ml of water were placed in a bioreactor, which was then autoclaved for 20 min at 121° C. to effect liquefaction. Then, 95 g of a hydrolyzed corn steep liquor, a 200 ml inoculum of the mixed culture LBM5, and 0.95 ml of a glucoamylase solution (EBS, G-ZYME G-990, nominal activity=200 U/ml) were added to the bioreactor to effect simultaneous saccharification and fermentation at 42° C. The pH of the medium was 6.3 initially and was later controlled at 5.5 by addition of 10 N NaOH. The time course of the simultaneous saccharification and fermentation is shown in Table 3 below.

TABLE 3

| Time (hr) | [lactic acid] (g/L) | [acetic acid] (g/L) | [glucose] (g/L) | [TRS] (g/L) |
|---|---|---|---|---|
| 0.0 | 5.2 | 0.5 | 24.0 | 67.8 |
| 2.0 | 6.7 | 0.6 | 30.0 | — |
| 4.0 | 8.1 | 0.9 | 46.2 | — |
| 24.5 | 65.4 | 1.1 | 53.6 | — |
| 26.5 | 72.9 | 1.1 | 37.3 | — |
| 29.5 | 78.3 | 1.2 | 28.5 | — |
| 46.5 | 108.5 | 1.4 | 15.5 | — |
| 50.5 | — | 1.5 | 19.4 | 22.1 |
| 54.5 | 116.0 | 1.5 | 13.0 | 19.9 |
| 70.8 | 120.5 | 1.5 | 5.3 | 9.6 |

EXAMPLE 8

A continuous cell-recycle fermenter was set-up as follows. A 2.5-liter stirred tank fermenter and a cross-flow microfiltration or ultrafiltration device were connected by a recirculating loop that drew the fermenter broth into the inlet of the filtration device. The outlet for retentate, which contained cell mass, was connected back to the fermenter, while the outlet for filtrate, which was a cell-free broth, was connected to a product reservoir via a pump controlled by a level controller. The level controller activated the filtrate pump when the fermentation broth raised to a set level, to maintain a constant working volume. The fermentation pH was maintained at the set point by addition of 10 N NaOH. The total working volume of the fermenter was maintained at 1200 ml, including the recycle loop hood-up volume.

In a continuous fermentation of *L. delbrueckii* subsp. *lactis* with a potato hydrolysate supplemented with 3.8% (v/v) hydrolyzed corn steep liquor as the feed, a steady state was obtained at pH 5.8, 37° C., and a dilution rate of 0.05 $h^{-1}$. The glucose concentration in the feed was 120 g/L. At the steady state, the lactic acid, glucose, and TRS concentrations in the broth filtrate were 93.3, 0.6, and 6.9 g/L, respectively. The cell concentration in the fermenter was 20 g/L.

EXAMPLE 9

A continuous cell-recycle fermenter was set-up as in Example 8. A continuous fermentation of the STLM-B medium by the mixed culture LBM5 was performed. The fermentation temperature was 42° C. and pH was maintained at 5.5 by addition of 5 N NaOH. With 110 g/L of glucose in the feed, a stable steady state was achieved at a dilution rate of 0.05 $h^{-1}$, resulting in a productivity of 5.7 g/(L•hr) at a lactic acid concentration of 90 g/L. The sugar impurities levels in the product were 0.03 g/L glucose and 2 g/L TRS. The cell concentration was 30 g/L. The bioreactor was operated for 527 hours without contamination.

EXAMPLE 10

A fermentation broth was obtained from lactic acid fermentation using potato hydrolysate as the carbon source and corn steep liquor as the nutrient supplement. The fermentation broth contained 119.3 g/L sodium lactate (i.e., equivalent to 94.8 g/L lactic acid) and 9.9 g/L TRS. The electrodialysis system employed a stack manufactured by Ionics. The stack consisted of 4 cells, each containing a pair of electrodes and 4 compartments (catholyte, feed, product, and anolyte, respectively) divided by three ion-exchange membranes (in the sequence of cation-, anion-, and cation-exchange membranes). The total effective membrane transfer area of the stack was 928 $cm^2$.

The operation of the electrodialysis system was carried out in the batch mode. At the beginning of each run, 2 liters of 1% NaOH and 2 liters of 1% $H_2SO_4$ were placed into the catholyte and anolyte reservoirs, respectively. Also, the fermentation broth and a 1% lactic acid solution (volumes as specified below) were placed into the feed and product reservoirs, respectively. The process streams were recirculated through the stack and a D.C. power was applied. A constant current was maintained throughout the course of the run. The voltage required to sustain the current was constant initially and increased rapidly as the sodium lactate concentration in the feed stream dropped below a critical value. The run was terminated when the desirable current could no longer be sustained by a voltage below a given maximum. Results of several runs under various operating conditions are summarized in Table 4 below.

TABLE 4

| Run # | $V_{f,i}$ (ml) | $V_{p,i}$ (ml) | i (mA/cm$^2$) | Y (%) | [LacH]$_p$ (g/L) | [NaOH]$_c$ (N) | [TRS]$_p$ (g/L) |
|---|---|---|---|---|---|---|---|
| 1 | 1500 | 1500 | 10.8 | 99 | 72.0 | 0.95 | 1.32 |
| 2 | 1500 | 1500 | 21.6 | 97 | 68.4 | 0.92 | 1.23 |
| 3 | 1500 | 500 | 10.8 | 99 | 124.0 | 0.98 | 1.96 |
| 4 | 1500 | 500 | 21.6 | 95 | 119.0 | 0.89 | 2.41 |
| 5 | 3000 | 500 | 21.6 | 95 | 137.0 | 1.46 | 4.80 |
| 6 | 1500 | 500 | 16.2 | 97 | 117.0 | 0.91 | 1.88 |

$V_{f,i}$ = initial volume of the feed stream, $V_{p,i}$ = initial volume of the product stream, i = current density, Y = yield of recovery, [LacH]$_p$ = final lactic acid concentration in the product stream, [NaOH]$_c$ = final sodium hydroxide concentration in the catholyte stream, and [TRS]$_p$ = final TRS concentration in the product stream.

Electrodialysis successfully converted sodium lactate into lactic acid and sodium hydroxide with a good yield of recovery. The lactic acid recovered was partially purified, as indicated by the TRS concentration. The obtainable lactic acid concentration was strongly affected by the ratio of volumes of feed and product streams initially charged to the system. The obtainable sodium hydroxide, similarly, was affected by the ratio of the initial feed and catholyte stream volumes.

EXAMPLE 11

An experiment was carried out to extract lactic acid from a crude acid solution which was prepared by vacuum evaporation of the pooled crude lactic acid solutions produced by electrodialysis in Example 10. Two extractants, A) 40% (v/v) tri-n-octyl amine in 2-heptanone and B) 40% (v/v) tri-n-octyl amine in 1-octanol, were used. The process was carried out at room temperature by extracting 22 ml of the crude acid with 55 ml of the extractant, separating the organic and aqueous phases, and back-extracting the organic solvent with 20 ml of a 3 N NaOH solution. There was no phase separation problems in either the extraction or the back-extraction step. The initial crude acid solution contained 320 g/L lactic acid and 7.8 g/L TRS. The back-extraction product, using solvent A, contained 230 g/L lactic acid (in the form of sodium lactate) and 0.52 g/L TRS. Over 90% of the total reducing sugars were removed by the extraction/back-extraction process. Similarly, solvent B yielded a back-extraction product that contained 237 g/L lactic acid and 0.52 g/L TRS.

EXAMPLE 12

Phase separation during extraction was examined using the fermentation broth that was used as the feed stream of electrodialysis in Example 10. The broth was acidified with sulfuric acid to pH below 2, which resulted in precipitation of denatured proteins. After centrifugal separation of the proteins, a clear supernatant was obtained. 15 ml of the supernatant was brought into contact with 3 ml of the extractant (40% tri-n-octyl amine in 2-heptanone) in a separatory funnel. The funnel was then placed on a ringstand for phase separation. After 10 minutes, the organic-continuous phase was still filled with emulsions and no clear organic layer was observed.

Phase separation was also examined for a crude lactic acid, which was obtained by vacuum evaporation of the pooled crude lactic acid solutions produced by electrodialysis in Example 10. 50 ml of the crude acid solution and 10 ml of the extractant were brought into contact in a separatory funnel. After 10 minutes of settling, a satisfactory phase separation was obtained. Electrodialysis processing followed by vacuum evaporation appeared to be effective in eliminating the phase separation problem in the subsequent extraction step.

EXAMPLE 13

A concentrated (by evaporation) and acidified fermentation broth, containing 140 g/L lactic acid and 12% TRS/LacH was processed via methyl esterification, hydrolysis, and distillation, to obtain a purified lactic acid. The purified product contained a total acidity of 0.53 N and a TRS concentration of 0.075 g/L, resulting in a TRS/LacH of 0.16% which was two orders-of-magnitude lower than the initial value.

Another crude fermentation broth, which was obtained by vacuum evaporation of the pooled crude lactic acid solutions produced by electrodialysis in Example 10, was purified similarly. The crude broth contained 320 g/L lactic acid and 2.4% TRS/LacH. The purified product contained 170 g/L of lactic acid and a TRS/LacH of 0.055%. A test tube containing 3 ml of the purified lactic acid was heated in a dry bath with the temperature initially set at 60° C. and gradually increased to 145° C. over three and half hours. The temperature was then maintained at 145° C. for 75 minutes before the tube was removed from the heated bath. The sample that remained in the tube was a slightly yellowish viscous liquid. By the extent of color formation, the heat-stability of this sample was much better than a commercial food-grade fermentation lactic acid and comparable to a commercial heat-stable grade fermentation lactic acid that is known to be suitable for polymer synthesis.

What is claimed is:

1. A method of converting starch in a mixture to glucose and glucose to lactic acid, comprising:
   (a) providing an ungelatinized and nonliquified starch-containing material; and
   (b) performing a combination step of gelatinizing and liquifying said starch by
      (1) adding an amount of α amylase enzyme to said starch-containing material effective to cause gelafinization and liquefaction of said starch-containing material during said combination step;
      (2) adding a stabilizing ion to form a starch containing material mixture;
      (3) maintaining said starch-containing material mixture at a pH in the range of about 4 to 7;
      (4) heating said starch-containing material mixture to a first elevated temperature of about 90°– 130° C.;
      (5) maintaining said starch-containing material mixture at said elevated temperature without enzyme deactivation;
      (6) cooling the temperature of said starch-containing material mixture to a second elevated temperature which is below the temperature used in step (4) and above about 50° C.; and
      (7) adjusting the pH to below about 6.5;
   (c) adding an effective amount of glucoamylase to said material mixture and maintaining said glucoamylase and said material mixture at the aforesaid conditions in said steps b(6) and b(7) without glucoamylase deactivation to produce said glucose; and
   (d) simultaneously with said step (c) adding a mixed culture containing *L. delbruecki* subsp. *lactic* ATCC 12315, *L. Casei* NRRLB-1445, *L. delbruecki* NRLLB-445, *L. Helveticus* NRRLB-1937 and *L. Casei* NRRLB-1922 to form a fermentation broth to effect conversion of said glucose to lactic acid.

2. The process of claim 1, wherein the α-amylase enzyme is added in a concentration of from about 0.5x to about 1000x, wherein x=30 units, U, of α-amylase enzyme/gram of dry substance of starch-containing material mixture and the glucoamylase enzyme is added in a concentration of 0.5x to 100x, wherein 1x=((13.44 unit-hour of glucoamylase)/ (gram of dry substance of said starting starch-containing material)) divided by the total hours of incubation.

3. The process of claim 1, wherein the glucoamylase-containing material mixture is maintained at the specified conditions under said step (c) for a time period of about 4 to 24 hours.

4. The process of claim 3, wherein the second elevated temperature is about 50° to 70° C., the pH is less than about 5.5 and the material is maintained at said temperature and pH for a time of from about 4 hours to about 8 hours.

5. A method of converting starch in a mixture to glucose and glucose to lactic acid, comprising:
   (a) providing an ungelafinized and nonliquified starch-containing material; and
   (b) performing a combination step of gelatinizing and liquifying said starch by
      (1) adding an amount of α amylase enzyme to said starch-containing material effective to cause gelatinization and liquefaction of said starch-containing material during said combination step;
      (2) adding a stabilizing ion to form a starch-containing material mixture;
      (3) maintaining said starch-containing material mixture at a pH in the range of about 4 to 7;
      (4) heating said starch-containing material mixture to a first elevated temperature of about 90°–130° C. without enzyme deactivation;
      (5) cooling the temperature of said starch-containing material mixture to a second elevated temperature which is below the temperature used in step (4) and above about 50° C.; and
      (6) adjusting the pH to below about 6.5;
   (c) adding an effective amount of glucoamylase to said material mixture and maintaining said glucoamylase and said material mixture at the aforesaid conditions in said steps (b)(5) and (b)(6) without glucoamylase deactivation to produce said glucose;
   (d) adding nutrients to said material mixture; and
   (e) simultaneously with said step (d) adding a mixed culture containing *L. delbruecki* subsp. *lactic* ATCC 12315, *L. Casei* NRRLB-1445, *L. delbruecki* NRLLB-445, *L. Helveticus* NRRLB-1937 and *L. Casei* NRRLB-1922 to said material mixture to form a fermentation broth to effect conversion of said glucose to lactic acid.

6. The method of claim 5, wherein the glucose is fermented about 24 to 48 hours to convert greater than about 95% of said glucose to lactic acid.

7. The method of claim 5, wherein the fermentation is conducted in a fermenter and wherein the fermentation is continuous to produce a broth containing sodium lactate and wherein separation of the sodium lactate from the fermentation broth produces sodium hydroxide that is recycled to the fermenter and also produces lactic acid.

8. A method of converting starch to lactic acid comprising the steps of:
   (a) providing a liquified starch containing material as a feed stream, wherein said liquified starch containing material is produced by contacting with α-amylase;
   (b) converting said feed stream to glucose, by contacting with glucoamylase; and
   (c) adding a combination of microorganisms to a fermentation broth for fermenting glucose to lactic acid, wherein said combination is a mixed culture of *L. delbruecki* subsp. *lactic* ATCC 12315, *L. casei* NRRLB-1445, *L. delbruecki* NRLLB-445, and *L. helveticus* NRRLB-1937.

9. The method as defined in claim 8 wherein said combination further includes *L. casei* NRRLB-1922.

10. The method as defined in claim 8 further including the step of adding a nutrient to said fermentation broth.

11. The method as defined in claim 8 wherein fermentation pH is controlled by adding an alkali to said fermentation broth.

12. The method as defined in claim 8 further including the step of performing electrodialysis on said lactic acid produced by said step (c).

13. The method as defined in claim 12 wherein said lactic acid recovered by said electrodialysis step is concentrated by evaporation.

14. The method as defined in claim 13 further including the steps of liquid-liquid extraction and back extraction of said concentrated lactic acid.

15. The method as defined in claim 13 further including the step of esterification of said lactic acid after evaporation.

16. The method as defined in claim 8 wherein said fermentation step (c) is a continuous processing step.

* * * * *

UNITED STATES PATENT AND TRADEMARK OFFICE
CERTIFICATE OF CORRECTION

PATENT NO. : 5,464,760
DATED : November 7, 1995
INVENTOR(S) : Tsai, et al.

It is certified that error appears in the above-identified patent and that said Letters Patent is hereby corrected as shown below:

Col. 5, line 3, omit "mixtures" and insert --minutes--;

Col. 5, line 56, omit "awl" and insert --an--;

Col. 12, line 44, omit "gelafinization" and insert --gelatinization--;

Col. 13, line 23, omit "ungelafinized" and insert --ungelatinized--.

Signed and Sealed this

Third Day of September, 1996

Attest:

BRUCE LEHMAN

Attesting Officer

Commissioner of Patents and Trademarks